United States Patent
Khandelwal et al.

(10) Patent No.: US 12,338,215 B2
(45) Date of Patent: Jun. 24, 2025

(54) PROCESS AND APPARATUS FOR PREPARING PURIFIED STYRENE COMPOSITION USING DIVIDED-WALL COLUMN AND CRYSTALLIZATION UNIT

(71) Applicant: SULZER MANAGEMENT AG, Winterthur (CH)

(72) Inventors: Rahul Khandelwal, Katy, TX (US); Joseph C. Gentry, Houston, TX (US); Erik Temmel, Basel (CH); Manfred Stepanski, Buchs (CH)

(73) Assignee: Sulzer Management AG, Winterthur (CH)

( * ) Notice: Subject to any disclaimer, the term of this patent is extended or adjusted under 35 U.S.C. 154(b) by 15 days.

(21) Appl. No.: 18/029,595

(22) PCT Filed: Sep. 28, 2021

(86) PCT No.: PCT/EP2021/076672
§ 371 (c)(1),
(2) Date: Mar. 30, 2023

(87) PCT Pub. No.: WO2022/069479
PCT Pub. Date: Apr. 7, 2022

(65) Prior Publication Data
US 2023/0365480 A1    Nov. 16, 2023

(30) Foreign Application Priority Data
Oct. 7, 2020    (EP) ...................................... 20200620

(51) Int. Cl.
*C07C 7/04*    (2006.01)
*B01D 3/14*    (2006.01)
(Continued)

(52) U.S. Cl.
CPC ................ *C07C 7/14* (2013.01); *B01D 3/141* (2013.01); *B01D 9/0059* (2013.01); *C07C 7/04* (2013.01); *B01D 2009/0086* (2013.01)

(58) Field of Classification Search
CPC .... B01D 3/14; B01D 9/00; C07C 7/04; C07C 7/14
See application file for complete search history.

(56) References Cited

U.S. PATENT DOCUMENTS 2,389,793 A * 11/1945 Livingston ................ C07C 7/04
585/815
7,956,157 B2 * 6/2011 Butler .................... B01D 3/141
203/99
(Continued)

FOREIGN PATENT DOCUMENTS

CN    101723793 A    6/2010
CN    102272076 A    12/2011
(Continued)

OTHER PUBLICATIONS

European Search Report issued Mar. 10, 2021 in corresponding European Application No. 20200620.1.
(Continued)

*Primary Examiner* — Sharon Pregler
(74) *Attorney, Agent, or Firm* — Global IP Counselors, LLP

(57) ABSTRACT

A method for preparing a purified styrene composition includes providing a crude hydrocarbon composition containing styrene, subjecting the crude hydrocarbon composition to a distillation in a divided-wall column to produce an overhead hydrocarbon stream, a bottom hydrocarbon stream and a side hydrocarbon stream and subjecting the side hydrocarbon stream to at least one crystallization step to obtain a purified styrene composition.

18 Claims, 3 Drawing Sheets

(51) Int. Cl.
     *B01D 9/00*           (2006.01)
     *C07C 7/14*           (2006.01)

(56)               References Cited

U.S. PATENT DOCUMENTS

| | | |
|---|---|---|
| 8,153,853 B2 | 4/2012 | Butler |
| 10,604,458 B2 * | 3/2020 | Detjen .............. B01D 53/1425 |
| 2009/0306445 A1 | 12/2009 | Gehrke |
| 2017/0107167 A1 | 4/2017 | Faessler et al. |
| 2019/0022553 A1 * | 1/2019 | Sreenivasan ......... B01D 9/0013 |

FOREIGN PATENT DOCUMENTS

| | | |
|---|---|---|
| EP | 2952237 A1 | 12/2015 |
| JP | S61-218535 A | 9/1986 |
| JP | 2008-543893 A | 12/2008 |
| JP | 2012-513999 A | 6/2012 |
| WO | 2010/078098 A1 | 7/2010 |

OTHER PUBLICATIONS

International Search Report and Written Opinion issued Dec. 23, 2021 in corresponding International Application No. PCT/EP2021/076672.
International Preliminary Examination Report on Patentability issued Apr. 13, 2023 in corresponding International Application No. PCT/EP2021/076672.
Chinese First Office Action in 202180066332.8, dated Oct. 31, 2024 (EN Translation, CN Office Action) (41 pages).

\* cited by examiner

PROCESS AND APPARATUS FOR PREPARING PURIFIED STYRENE COMPOSITION USING DIVIDED-WALL COLUMN AND CRYSTALLIZATION UNIT

CROSS-REFERENCE TO RELATED APPLICATION

This application is a U.S. National Stage application of International Application No. PCT/EP2021/076672, filed Sep. 28, 2021, which claims priority to European Application No. 20200620.1, filed Oct. 7, 2020 and U.S. Provisional Application No. 63/085,760, filed Sep. 30, 2020, the contents of each of which are hereby incorporated by reference.

BACKGROUND

Technical Field

The present invention relates to a method for preparing a purified styrene composition from a crude hydrocarbon composition containing styrene as obtained from a pyrolytic or catalytic based waste polystyrene depolymerization unit. Moreover, the present invention relates to a plant, in which the method may be performed.

Background of the Invention

Styrene is an important building block for polymers, such as polystyrene, acrylonitrile-butadiene-styrene (ABS)/styrene-acrylonitrile (SAN) resins, styrene butadiene (SB) copolymer latexes, unsaturated polyester resins, styrene-butadiene rubber (SBR) elastomers and latexes. It is one of the highest volume commodity chemicals traded, and over 30% of annual styrene production is traded internationally. Predominantly, styrene is produced starting with raw materials benzene and ethylene. Benzene is alkylated to produce ethylbenzene (EB), and the EB is converted into styrene via the conventional dehydrogenation process or ethyl-benzene/styrene monomer (EBSM) process, respectively, or the propylene oxide/styrene monomer (POSM) process. Typically, styrene plants are located near ethylene crackers due to the gaseous nature of ethylene which makes it relatively difficult to transport as compared to benzene.

Apart from the on-purpose production route via EBSM/POSM, styrene is also present in hydrocarbon streams, such as pyrolysis gasoline obtained from steam cracking of naphtha, hydrocarbon fraction obtained from waste polystyrene pyrolysis or catalysis, gas oils etc. Styrene extraction from these hydrocarbon streams, although far less in quantity as compared to EBSM/POSM, can be an attractive economic opportunity to the operator due to the low feedstock cost. The area of styrene production from waste polystyrene has especially gained mainstream attention due to the plastics recycling issues being encountered in the world presently. Waste plastics pose a serious threat to the environment. However, this separation is technically difficult due to the presence of close boiling molecules and impurities coming from the starting feedstock. For instance, during polystyrene recycling different sorts of waste polystyrene are fed into the catalytic or pyrolysis reactor. Due to the contamination of the waste plastic coupled with production of other close boiler compounds, like benzene, toluene, ethylbenzene, alpha-methyl styrene, cumene, n-propyl benzene etc., produced during the pyrolytic or catalytic step there is a need to have a reliable method to purify this styrene oil to the final ASTM grade styrene specification.

However, removal of close boiling molecules, such as mixed xylenes, ethylbenzene, etc., from styrene by normal distillation is an energy intensive process. More specifically, conventional two or three column approaches, such as employed in EBSM derived styrene purification, are not only energy intensive and require a high capital expenditure (CAPEX), but also fail to remove close boiling impurities, like oxygenates, color causing compounds, sulfur species etc. Oxygenates can not only come from the feedstock, but are also produced in the process due to air leakages since these columns are in deep vacuum service (typically about 100 to 300 mbar range). It is a known phenomenon that styrene reacts with oxygen to form oxygenate species, like benzaldehyde, which can violate the Total aldehyde as Benzaldehyde specification. Further, because the source to pyrolytic or catalytic reactor is waste polystyrene, which is sorted from mixed plastics, there is a potential, despite exercising control of feedstock input to catalytic or pyrolytic depolymerization reactor, for nitrogenated and chlorinated species also being present in the crude styrene oil produced from depolymerization of waste polystyrene. Such species are considered as bad contaminants for the styrene polymerization process, which is the eventual goal of establishing a true circular economy concept in styrene.

Considering the above, the objective underlying an embodiment of the present invention is to provide an energy efficient method requiring only a plant with low CAPER for preparing a purified styrene composition from a styrene containing feed composition from a styrene containing stream produced by pyrolysis of recycled polystyrene or the like, which reliably and efficiently removes impurities, such as color inducing species, sulfur and oxygenates, ethylbenzene, mixed xylenes, propylbenzene, ethyl toluene, alpha-methylstyrene, nitrogenated and chlorinated molecules etc., from the styrene in an energy efficient manner, even if the impurities are contained in a comparable high amount in the styrene containing feed composition, so as to obtain, in a cost efficient manner, a very pure styrene composition.

SUMMARY

In accordance with an embodiment of the present invention, this object is satisfied by providing a method for preparing a purified styrene composition, wherein the method comprises the following steps:
a) providing a crude hydrocarbon composition containing styrene,
b) subjecting the crude hydrocarbon composition provided in step a) to a distillation in a divided-wall column so as to produce an overhead hydrocarbon stream, a bottom hydrocarbon stream and a side hydrocarbon stream and
c) subjecting the side hydrocarbon stream obtained in step b) to at least one crystallization step so as to obtain a purified styrene composition.

This solution bases on the surprising finding that by first subjecting a crude hydrocarbon composition containing styrene to a distillation in a divided-wall column so as to produce an overhead hydrocarbon stream, a bottom hydrocarbon stream and a side hydrocarbon stream and then subjecting the side hydrocarbon stream obtained in step b) to at least one crystallization step, not only impurities, such as close boiling color inducing species, sulfur and oxygenates, ethylbenzene, mixed xylenes, propylbenzene, ethyltoluene, alpha-methylstyrene, nitrogenated and chlorinated molecules etc., are reliably and completely or at least nearly completely removed from styrene, even if the impurities are contained in a comparable high amount in the crude hydrocarbon composition, but that the respective process is in addition thereto energy efficient and only requires a plant with comparable low CAPEX. This can be neither achieved by using two or three distillation columns for purifying the crude hydrocarbon stream according to the prior art. Crystallization, on a standalone basis, can remove some, not all, of these impurities directly from the crude styrene oil but the diluted styrene poses very low temperature requirements along with addition of significant purification and residue stages making the solution ineffective. CAPEX and operating expenditure prohibitive. The combination of first subjecting a crude hydrocarbon composition to a distillation in a divided-wall column and then subjecting the side hydrocarbon stream obtained in the divided-wall column to at least one crystallization step overcomes the challenges listed above. More specifically, in the typical approach of using two distillation columns for purifying the crude hydrocarbon stream, the distillation energy requirement is disproportionate between the two distillation columns so that replacing the two distillation columns by a divided-wall column is not at all reasonable. Furthermore, this replacement would not at all solve the problem of removal of close boiling color inducing species, oxygenates, sulfur species, nitrogenated and chlorinated species etc., since these impurities cannot be removed in a desirable high degree from styrene by distillation. In contrast thereto, an embodiment of the present invention relies on the "slipping" of impurities, like ethylbenzene, through the distillation step to an extent that the energy consumption of two separate distillation columns becomes more or less the same or at least essentially the same. In other words, instead of producing by distillation an ultra-pure styrene stream containing for instance 99.8% by weight styrene, the process of an embodiment of the present invention intentionally produces by distillation a less pure styrene stream containing for instance 99.2% by weight styrene, thus letting intentionally "slip" the close boiling point impurities through the distillation step. On account of this reason, the two distillation columns become an excellent case for replacement by a divided-wall column, thus achieving 30% energy and 25% CAPEX savings compared to the conventional plants making use of two separate distillation columns. The so obtained pre-purified styrene stream, which is the side hydrocarbon stream of the divided-wall column obtained in step b), containing the impurities, like color inducing species, oxygenates, ethylbenzene and sulfur species, which are not completely removable by distillation, is then subjected to at least one crystallization step, which not only upgrades the styrene content in the purified styrene composition from say 99.2% by weight to more than 99.8% by weight styrene, but which also removes the close boiling and difficult or unable to be removed by conventional distillation impurities from the purified styrene composition. Thus, for instance ASTM grade styrene may be easily and energy efficiently be produced from a polystyrene derived crude styrene oil. All in all, the process in accordance with an embodiment of the present invention allows to cost efficiently purify a styrene containing composition from impurities and even from impurities having a boiling point close to that of styrene.

As known in the art, crystallization processes or steps, respectively, may be typically carried out in multiple stages, i.e. in several crystallization stages. In view of this, in the present application a crystallization step or section is defined as comprising one or more crystallization stages.

An embodiment of the present invention is not particularly limited concerning the styrene content of the crude hydrocarbon composition provided in step a). Good results are in particular obtained, when the crude hydrocarbon composition provided in step a) contains at least 10% by weight, preferably 30% by weight, preferably at least 50% by weight, still more preferably at least 60% by weight, yet more preferably at least 70% by weight and most preferably at least 80% by weight of styrene.

In principle, the divided-wall column used in step b) may be any divided-wall column and in particular a top divided-wall column, a middle-divided wall column or a bottom-divided wall column. In a top divided-wall column, the dividing wall extends from the top of the column (to which the wall is connected) downwards over a part of the height of the divided wall column, whereas in a bottom divided-wall column the dividing wall extends from the bottom of the column (to which the wall is connected) upwards over a part of the height of the divided wall column. In contrast thereto, in a middle divided-wall column the dividing wall extends over a part of the height of the divided wall column, but without being connected with the top or bottom, thus having a distance to the top as well as to the bottom of the divided-wall column.

In accordance with a particular preferred embodiment of the present invention, the crude hydrocarbon composition provided in step a) is subjected in step b) to a distillation in a middle divided-wall column.

Good results are in particular obtained, when the dividing wall of the middle divided-wall column extends, seen over the height, which is the straight distance between the bottom and the top of the middle divided-wall column, from 10 to 90%, preferably from 20 to 80%, more preferably from 30 to 70% and most preferably from 40 to 60% of the height of the middle divided-wall column. In other words, the dividing wall of the middle divided-wall column has a distance to the top as well as to the bottom of the middle divided-wall column, independently from each other, of at least 10% or of at least 20% or of at least 30% or of at least 40%.

In a further development of the idea of an embodiment of the present invention, it is proposed that the dividing wall extends in the middle divided-wall column essentially vertically downwards, wherein essentially vertically downwards means that the angle between the dividing wall and the length axis of the middle divided-wall column is at most 20°, preferably at most 10°, more preferably at most 5° and most preferably 0°.

Moreover, it is preferred that the crude hydrocarbon composition, the divided-wall column and the operation conditions are adjusted so that the overhead hydrocarbon stream obtained in step b) is a $C_{7-}$-hydrocarbon stream, the bottom hydrocarbon stream obtained in step b) is a $C_{9+}$-hydrocarbon stream and the side hydrocarbon stream obtained in step b) is a styrene containing hydrocarbon stream, i.e. a styrene containing $C_8$-hydrocarbon stream.

As set out above, it is intended that the distillation in step b) is performed so that a pre-purified styrene containing $C_8$-hydrocarbon stream is obtained as side hydrocarbon stream, but not an ultra-pure styrene containing $C_8$-hydrocarbon stream is obtained as side hydrocarbon stream, in order to adjust the energy consumption of both parts of the divided-wall column, which are separated by the dividing wall, so as to have about the same energy consumption. This is possible, since according to an embodiment of the present invention the remaining impurities and in particular impurities having a boiling point close to that of styrene are separated from the side hydrocarbon stream obtained in step b) by the subsequent at least one crystallization step c).

In view of this, it is preferred that the side hydrocarbon stream obtained in step b) and subjected in step c) to at least one crystallization step contains at least 80% by weight, preferably at least 90% by weight, more preferably at least 98% by weight and most preferably at least 99% by weight of styrene, but preferably less than 99.8% by weight of styrene, preferably less than 99.5% by weight of styrene and more preferably less than 99.3% by weight of styrene.

As set out above, an embodiment of the present invention is particularly suitable for purifying a crude hydrocarbon composition containing styrene, which contains as impurities one or more impurities selected from the group consisting of color inducing species, sulfur species, meta- and ortho-xylenes, ethylbenzene, phenylacetylene, cumene, n-propylbenzene, alpha-methylstyrene, ethyltoluene, organo-chlorinated, organo-nitrogenated species and arbitrary mixtures of two or more of the aforementioned impurities. Suitable examples therefore are one or more sulfur species and preferably one or more sulfur species selected from the group consisting of mercaptans, disulfides, thiophenes having a boiling point of 130 to 150° C. and arbitrary combinations of two or more thereof. Other suitable examples therefore are one or more color inducing species comprising at least one of conjugated diolefins, oxygenated species and oxygenated sulfur species. For instance, the oxygenated species may be water, an alcohol, a ketone and/or a aldehyde, whereas fulvenes and their derivatives are suitable examples for diolefins.

Preferably, the total content of the aforementioned impurities in the crude hydrocarbon composition is 1 to 60% by weight and more preferably 1 to 40% by weight.

As set out above, it is intended that after the distillation in step b) in the pre-purified styrene containing $C_8$-hydrocarbon stream, which is obtained as side hydrocarbon stream, still impurities and in particular the aforementioned impurities are contained to a certain extent. Therefore, it is preferred according to an embodiment of the present invention that also the side hydrocarbon stream obtained in step b) and subjected to distillation in step c) contains one or more of the aforementioned impurities, i.e. impurities selected from the group consisting of color inducing species, sulfur species, meta- and ortho-xylenes, ethylbenzene, phenyl acetylene, cumene, n-propylbenzene, alpha-methylstyrene, ethyltoluene, organo-chlorinated, organo-nitrogenated species and arbitrary mixtures of two or more of the aforementioned impurities. Preferred impurities are one or more sulfur species and preferably one or more sulfur species selected from the group consisting of mercaptans, disulfides, thiophenes having a boiling point of 130 to 150° C. and arbitrary combinations of two or more thereof, and/or one or more color inducing species comprising at least one of conjugated diolefins, oxygenated species, and oxygenated sulfur species, such as water, one or more alcohols, one or more ketones, one or more aldehydes, one or more fulvenes and arbitrary combinations of two or more thereof.

Preferably, the total content of the aforementioned impurities in the side hydrocarbon stream obtained in step b) and subjected to distillation in step c) is 0.1 to 10% by weight and more preferably 0.7 to 5% by weight.

Concerning the kind of crystallization technique, an embodiment of the present invention is not particularly limited. Thus, the at least one crystallization step preferably comprises at least one static crystallization stage and/or at least one dynamic crystallization stage and more preferably at least one static melt crystallization stage and/or at least one dynamic melt crystallization stage.

In accordance with a particular preferred embodiment of the present invention, the at least one crystallization step comprises at least one static melt crystallization stage and at least one dynamic melt crystallization stage.

Good results are in particular obtained, when the at least one dynamic crystallization stage is a falling film crystallization stage and more preferably a falling film melt crystallization stage. However, instead or in addition to a falling film crystallization stage also a suspension crystallization stage and more preferably a suspension melt crystallization stage may be used.

In a further development of the idea of an embodiment of the present invention, it is suggested that the method comprises a crystallization step, which comprises one to ten static crystallization stages and one to ten dynamic crystallization stages. Even more preferably, the method comprises a crystallization step, which comprises one to five static crystallization stages and one to five dynamic crystallization stages. If the method comprises two or more dynamic crystallization stages and/or two or more static crystallization stages, each of the dynamic crystallization stages is fluidly coupled with one or two other dynamic crystallization stages, each of the static crystallization stages is fluidly coupled with one or two other static crystallization stages and one of the dynamic crystallization stages is fluidly coupled with one of the static crystallization stages. In other words, the dynamic crystallization stages are arranged in series to each other, and the static crystallization stages are arranged in series to each other. The numbering starts from the static crystallization stage and the dynamic crystallization stage, which are fluidly coupled together. Thus, if the crystallization comprises four dynamic crystallization stages and four static crystallization stages, the first dynamic crystallization stage and the first static crystallization stage are those, which are coupled with each other. The first dynamic crystallization stage is fluidly coupled with the second dynamic crystallization stage, which is coupled with the third dynamic crystallization stage, wherein the third dynamic crystallization stage is coupled with the fourth dynamic crystallization stage. Likewise thereto, the first static crystallization stage is fluidly coupled with the second static crystallization stage, which is coupled with the third static crystallization stage, wherein the third static crystallization stage is coupled with the fourth static crystallization stage. In both series, the first crystallization stage is the most upstream crystallization stage, wherein the second, third and fourth crystallization stages are located downstream of the first crystallization stage in series to each other.

In accordance with a first particular preferred embodiment of the present invention, the method comprises a crystallization step, which comprises one static crystallization stage and one dynamic crystallization stage. In this variant, the side hydrocarbon stream obtained in step b) and subjected in step c) to the at least one crystallization step is preferably fed into the dynamic crystallization stage so as to produce a styrene enriched crystallized fraction and a styrene depleted residue fraction. The styrene depleted residue fraction obtained in the dynamic crystallization stage mainly contains the styrene depleted mother liquor and is fed into the static crystallization stage as mother liquor. Also, in the static crystallization stage a styrene enriched crystallized fraction and a styrene depleted residue fraction are produced, wherein the styrene enriched crystallized fraction obtained in the static crystallization stage is fed into the dynamic crystallization stage and mixed there with the side hydrocarbon stream fed into the dynamic crystallization stage. The styrene depleted residue fraction obtained in the static crystallization stage is withdrawn, whereas the styrene enriched crystallized fraction obtained in the dynamic crystallization stage is withdrawn as the purified styrene composition. In principle, the side hydrocarbon stream obtained in step b) may be alternatively to the above-described embodiment fed into the static crystallization stage, i.e. the static crystallization and dynamic crystallization stages may be arranged in reversed order to the aforementioned description. However, better results are obtained, when the side hydrocarbon stream obtained in step b) is fed into the dynamic crystallization stage. For the sake of completeness, it is noted that the aforementioned terms "styrene enriched crystallized fraction" and "styrene depleted residue fraction" are meant relative to the styrene content of the input into the respective crystallization stage and not relative to the styrene content of the side hydrocarbon stream obtained in step b). In other words, the styrene enriched crystallized fraction obtained in the static crystallization stage has a higher styrene content than the input into this static crystallization stage (which is the styrene depleted residue fraction fed from the dynamic crystallization stage into the static crystallization stage) and the styrene depleted residue fraction has a lower styrene content than the input into this static crystallization stage.

In accordance with a second particular preferred embodiment of the present invention, the method comprises a crystallization step, which comprises two to five (or a plurality of) static crystallization stages and two to five (or a plurality of) dynamic crystallization stages. Preferably, the side hydrocarbon stream obtained in step b) and subjected in step c) to the at least one crystallization step is fed into the first of the two to five dynamic crystallization stages so as to produce a first styrene enriched crystallized fraction and a first styrene depleted residue fraction, wherein the first styrene enriched crystallized fraction is fed into the second of the two to five dynamic crystallization stages, wherein in any of the second and of the optional third to fifth dynamic crystallization stages a styrene enriched crystallized fraction and a styrene depleted residue fraction is produced, wherein each of the styrene enriched crystallized fractions produced in the second and the optional third to fourth dynamic crystallization stages is fed into a downstream dynamic crystallization stage and each of the styrene depleted residue fractions produced in the second and the optional third to fifth dynamic crystallization stages is fed into an upstream dynamic crystallization stage. The first styrene depleted residue fraction is fed into the first of the two to five static crystallization stages so as to produce a second styrene enriched crystallized fraction and a second styrene depleted residue fraction, wherein the second styrene enriched crystallized fraction is fed into the first dynamic crystallization stage and the second styrene depleted residue fraction is fed into the second of the two to five static crystallization stages. In any of the second and of the optional third to fifth static crystallization stages a styrene enriched crystallized fraction and a styrene depleted residue fraction is produced, wherein each of the styrene depleted residue fractions produced in the second and the optional third to fourth static crystallization stages is fed into a downstream static crystallization stage and each of the styrene enriched crystallized fractions produced in the second and the optional third to fifth dynamic static stages is fed into an upstream static crystallization stage. In principle, the side hydrocarbon stream obtained in step b) and subjected in step c) to the at least one crystallization step may be fed into one of the static crystallization stages, i.e. the static crystallization and dynamic crystallization stages may be arranged in reversed order to the aforementioned description. However, better results are obtained, when the side hydrocarbon stream obtained in step b) is fed into one of the dynamic crystallization stage.

In an alternative variant to the aforementioned described variant, the side hydrocarbon stream obtained in step b) and subjected in step c) to the at least one crystallization step is fed into the second of the two to five dynamic crystallization stages and not into the first dynamic crystallization stage, wherein first to fifth is again seen in the direction upstream to down-stream. Again, the most upstream dynamic crystallization stage (i.e. the first dynamic crystallization stage) is that, which receives a styrene enriched crystallized fraction from the first static crystallization stage and from which a styrene depleted residue fraction is fed into the first static crystallization stage, whereas the most downstream dynamic crystallization stage is that, from which the purified styrene composition is withdrawn. Likewise, the most upstream static crystallization stage (i.e. the first static crystallization stage) is that, which receives a styrene depleted residue fraction from the first dynamic crystallization stage and from which a styrene enriched crystallized fraction is fed into the first dynamic crystallization stage, whereas the most downstream static crystallization stage (i.e. the second static crystallization stage) is that, from which the styrene depleted residue fraction is withdrawn.

For instance, the method comprises a crystallization step, which comprises two static crystallization stages and four dynamic crystallization stages. In this embodiment, the side hydrocarbon stream obtained in step b) and subjected in step c) to the at least one crystallization step is fed into the second of the dynamic crystallization stages so as to produce a second styrene enriched crystallized fraction and a second styrene depleted residue fraction. The second styrene enriched crystallized fraction is fed into the third of the four dynamic crystallization stages so as to produce a third styrene enriched crystallized fraction and a third styrene depleted residue fraction, wherein the third styrene enriched crystallized fraction is fed into the fourth of the dynamic crystallization stages so as to produce a fourth styrene enriched crystallized fraction and a fourth styrene depleted residue fraction. While the fourth styrene enriched crystallized fraction is withdrawn as purified styrene composition, the fourth styrene depleted residue fraction is fed into the third dynamic crystallization stage, the third styrene depleted residue fraction is fed into the second dynamic crystallization stage and the second styrene depleted residue fraction is fed into the first dynamic crystallization stage. In the first dynamic crystallization stage, a first styrene enriched crystallized fraction and a first styrene depleted residue fraction are produced. While the first styrene enriched crystallized fraction is fed into the second dynamic crystallization stage, the first styrene depleted residue fraction is fed into the first of the two static crystallization stages, in which a fifth styrene enriched crystallized fraction and a fifth styrene depleted residue fraction are produced. While the fifth styrene enriched crystallized fraction is fed into the first dynamic crystallization stage, the fifth styrene depleted residue fraction is fed into the second of the two static crystallization stages, in which a sixth styrene enriched crystallized fraction and a sixth styrene depleted residue fraction are produced. While the sixth styrene enriched crystallized fraction is fed into the first static crystallization stage, the sixth styrene depleted residue fraction is removed.

In all of the above described methods, preferably the production of a styrene enriched crystallized fraction and of a styrene depleted residue fraction in a crystallization stage comprises the steps of removing the remaining liquid from the crystallization stage as styrene depleted residue fraction after termination of the crystallization in the crystallization stage, of melting the crystal layer obtained in the crystallization stage and of withdrawing the obtained crystal melt as styrene enriched crystallized fraction from the crystallization stage.

In order to increase the purity of the purified styrene product, it is preferable to perform in any of the crystallization stages at least one sweating step before melting the crystal layers formed on the cooled surfaces of the crystallizer used in the single crystallization stages. Sweating means that the crystal layer deposited on the cooled surfaces are gently heated to a temperature close to the melting temperature of styrene in order to partially melt the crystals. Trapped and adherent melt, which contains the impurities, drains off during the partial melting of the crystals and is then removed from the crystallizer. In order to conduct such a sweating, the surface, on which the crystals are deposited, is heated with a heat transfer medium to the desired temperature. The sweating may be performed one or several times before melting the crystal layers deposited on the cooled surfaces. Thus, the sweating leads to one or more sweating fractions and to a purified crystal layer. Preferably, at least a portion of the first sweating fraction obtained thereby is fed to the remaining liquid which has been removed as styrene depleted residue fraction.

The crystallization temperature depends on the composition of the side hydrocarbon stream obtained in step b). However, good results are obtained, when at least one and preferably all of the at least one static melt crystallization stage and/or of the at least one dynamic melt crystallization stage are performed at a temperature of −200° C. and 30° C., preferably at a temperature of −140° C. and 0° C. and more preferably at a temperature of −100° C. and −30° C.

As set out above, an embodiment of the present invention is particularly suitable for purifying as crude hydrocarbon composition a pygas. In particular, pygas obtained by pyrolyzing recycled polystyrene is suitable as crude hydrocarbon composition. The process of the present invention allows to cost-efficiently purify styrene from such feed compositions, which is not possible with the prior art methods.

The method in accordance with an embodiment of the present invention results in a very pure styrene containing composition. Preferably, the purified styrene composition has a styrene content of at least 99.00% by weight, more preferably of at least 99.50% by weight, even more preferably of at least 99.80% by weight, still more preferably of at least 99.90% by weight, yet more preferably of at least 99.95% by weight and most preferably of at least 99.98% by weight.

In particular, the method in accordance with an embodiment of the present invention allows to completely or at least nearly completely remove color inducing species from the crude styrene containing composition. Therefore, in a further development of the idea of an embodiment of the present invention, it is proposed that the purified styrene composition has a color of maximum 15 as defined by Pt-Co scale as per ASTM D5386.

Furthermore, the method in accordance with an embodiment of the present invention allows to completely or at least nearly completely remove sulfur species from the crude styrene containing composition. Consequently, it is in particular preferred, when the purified styrene composition comprises less than 2 ppmw of total elemental sulfur as contained in mercaptans, disulfides and thiophenes and/or less than 20 ppmw of oxygenates.

In addition, the method in accordance with an embodiment of the present invention allows to obtain purified styrene composition, which comprises less than 40 ppmw of impurities selected from the group consisting of phenylacetylene, mixed xylenes, ethylbenzene, cumene, ethyltoluene, n-propylbenzene, and alpha-methylstyrene, and/or which has polymer content of less than 10 ppmw.

Preferably, the purified styrene composition has total organic chlorine content of less than 2 ppmw.

For instance, the purified styrene composition may meet the following specifications.

TABLE 1

| Parameter | Unit | Specification | Test Method |
|---|---|---|---|
| Color | Pt/Co scale | 15 max. | ASTM D5386 |
| Styrene monomer purity | Wt % | 99.8 min. | ASTM D5135 or 7504 |
| Aldehydes as benzaldehyde | Wt ppm | 75 max. | ASTM D2119 |
| Peroxides as $H_2O_2$ | Wt ppm | 15 max. | ASTM D2340 |
| Polymer content | Wt ppm | 10 max. | ASTM D2121 Test Method A |
| Inhibitor (tert-butylcatechol) | Wt ppm | 10 max. | ASTM D4590 |
| Ethylbenzene | Wt ppm | 500 max. | ASTM D5135 or D7504 |
| Benzene | Wt ppm | 1 max. | ASTM D6229 |
| Phenylacetylene | Wt ppm | 150 max. | ASTM D5135 |
| Water | Wt ppm | 50 max. | ASTM E1064 |
| Total organic Chlorides | Wt ppm | 2 max. | ASTM D5808 |
| Copper and Manganese | Wt ppm | 5 max. | UOP 389 or 407 |
| Viscosity at 25° C. | cP | 0.75 max | |
| Appearance | — | Clear, transparent liquid free of sediment and haze at 18 to 25° C. | |

According to a further aspect, an embodiment of the present invention relates to a plant for preparing a purified styrene composition comprising at least one divided-wall column and at least one crystallization block, wherein the divided-wall column comprises an inlet line for a crude hydrocarbon composition containing styrene, a line for overhead hydrocarbon stream, a line for bottom hydrocarbon stream and a line for a side hydrocarbon stream, wherein the at least one crystallization block comprises an inlet line, wherein the line for a side hydrocarbon stream of the divided-wall column leads to (or is connected with or is, respectively) the inlet line of the at least one crystallization block, and wherein preferably the at least one crystallization block comprises two or more static crystallization stages and two or more dynamic crystallization stages.

Preferably, the divided-wall column is a middle divided-wall column. Good results are in particular obtained, when the dividing wall of the middle divided-wall column extends, seen over the height, which is the straight distance between the bottom and the top of the middle divided-wall column, essentially vertically downwards from 10 to 90%, preferably from 20 to 80%, more preferably from 30 to 70% and most preferably from 40 to 60% of the height of the middle divided-wall column, wherein essentially vertically downwards means that the angle between the dividing wall and the length axis of the middle divided-wall column is at most 20°, preferably at most 10°, more preferably at most 5° and most preferably 0°.

In a further development of the idea of an embodiment of the present invention it is suggested that the plant further comprises a pyrolysis or catalytic reactor unit block comprising an inlet line and an outlet line, wherein the outlet line of the pyrolysis or catalytic reactor unit block leads into (or is connected with or is, respectively) the inlet line of the divided-wall column.

In accordance with a particular preferred embodiment of the present invention, the at least one crystallization block comprises:

at least one static crystallization section comprising two or more static crystallization stages, at least one dynamic crystallization section comprising two or more dynamic crystallization stages and at least two conduits that fluidly couple at least one of the two or more static crystallization stages with at least one of the two or more dynamic crystallization stages. Preferably, one of the at least two conduits fluidly couples one of the static crystallization stages with one of the dynamic crystallization stages so that a styrene depleted residue fraction obtained in the dynamic crystallization stage may be fed into the static crystallization stage being fluidly coupled with the dynamic crystallization stage, and one of the at least two conduits fluidly couples the static crystallization stage with the dynamic crystallization stage being fluidly coupled with the static crystallization stage so that a styrene enriched crystallized fraction obtained in the static crystallization stage may be fed into the dynamic crystallization stage, wherein each two of the remaining static crystallization stages are fluidly coupled with each other by means of at least two conduits, and wherein each two of the remaining dynamic crystallization stages are fluidly coupled with each other by means of at least two conduits.

The term "crystallization block" refers to an apparatus for a purification process with one or more crystallizers. Moreover, the term crystallization stage is not only used to denote a method step or stage, respectively, but also to denote an apparatus, namely that part of a crystallizer, in which a crystallization stage is performed. The crystallization stage as apparatus feature may be also designated as crystallizer, crystallizer unit or the like.

Preferably, the one or more static crystallization stages are static melt crystallization stages and the one or more dynamic crystallization stages are dynamic melt crystallization stages.

Preferably each of the dynamic crystallization stages is fluidly coupled with one or two other dynamic crystallization stages and each of the static crystallization stages is fluidly coupled with one or two other static crystallization stages.

Moreover, it is preferred that the at least one crystallization block comprises two to five static crystallization stages, two to five dynamic crystallization stages and at least two conduits that fluidly couple at least one of the two to five static crystallization stages with at least one of the two to five dynamic crystallization stages, wherein one of the at least two conduits fluidly couples one of the static crystallization stages with one of the dynamic crystallization stages so that a styrene depleted residue fraction obtained in the dynamic crystallization stage may be fed into the static crystallization stage being fluidly coupled with the dynamic crystallization stage, and wherein one of the at least two conduits fluidly couples the static crystallization stage with the dynamic crystallization stage being fluidly coupled with the static crystallization stage so that a styrene enriched crystallized fraction obtained in the static crystallization stage may be fed into the dynamic crystallization stage, wherein each two of the remaining static crystallization stages are fluidly coupled with each other by means of at least two conduits, and wherein each two of the remaining dynamic crystallization stages are fluidly coupled with each other by means of at least two conduits.

BRIEF DESCRIPTION OF THE DRAWINGS

In order that the manner in which the above recited and other advantages and objects of an embodiment of the invention are obtained, a more particular description of an embodiment of the invention briefly described above will be rendered by reference to specific embodiments thereof, which are illustrated, in the appended drawings. Understanding that these drawings depict only typical embodiments of the invention and are therefore not to be considered limiting of its scope, the invention will be described with additional specificity and detail through the use of the accompanying drawings in which:

FIG. 1 shows a plant 10 particularly suitable for purifying a styrene containing stream produced from a recycled polystyrene stream via pyrolysis. The plant 10 comprises a pyrolysis or catalytic reactor unit block 12, a divided-wall column 14 and a crystallization block 16. The pyrolysis or catalytic reactor unit block 12 comprises an inlet line 18 for feed, such as for a stream made of recycled polystyrene and an outlet line for pyrolysis product, which is simultaneously the inlet line 20 for crude hydrocarbon stream containing styrene. The divided-wall column 14 is a middle divided-wall column 14, wherein the dividing wall 28 of the middle divided-wall column 14 extends, seen over the height, Which is the straight distance between the bottom and the top of the middle divided-wall column 14, vertically downwards from about 25% to about 75% of the height of the middle divided-wall column. The divided-wall column 14 comprises a line 22 for overhead hydrocarbon stream, a line 24 for bottom hydrocarbon stream and a line 26 for side hydrocarbon stream, wherein the line 26 for side hydrocarbon stream is the inlet line to the crystallization block 16. The crystallization block 16 comprises a discharge conduit 30 for styrene depleted residue fraction and a discharge conduit 32 for purified styrene composition. The crystallization block 16 might be composed as that shown in FIG. 2 or that as shown in FIG. 3.

During the operation, the pyrolysis of polystyrene is performed in the pyrolysis or catalytic reactor unit block 12, which may be operated thermally or in a catalytic mode. The effluent from the pyrolysis or catalytic reactor unit block 12 contains styrene and a plurality of impurities and is fed via the line 20 as crude hydrocarbon stream containing styrene into the middle divided-wall column 14. In the middle divided-wall column 14, the mixture is divided into a $C_{9+}$-hydrocarbon stream obtained as bottom hydrocarbon stream and withdrawn via line 24, a $C_{7-}$-hydrocarbon stream obtained as top hydrocarbon stream and withdrawn via line 22 as well as a styrene containing $C_8$-hydrocarbon stream 26 obtained as side hydrocarbon stream and withdrawn via line 26. The side hydrocarbon stream is fed via line 26 into the crystallization block 16, where it is crystallized. During the crystallization, the impurities and in particular the color inducing species, sulfur species, oxygenates and impurities having a boiling point close to that of styrene, such as ethylbenzene, are reliably and nearly completely removed and withdrawn styrene depleted residue fraction via line 30, whereas the purified styrene composition is withdrawn via line 32.

Figure 1:
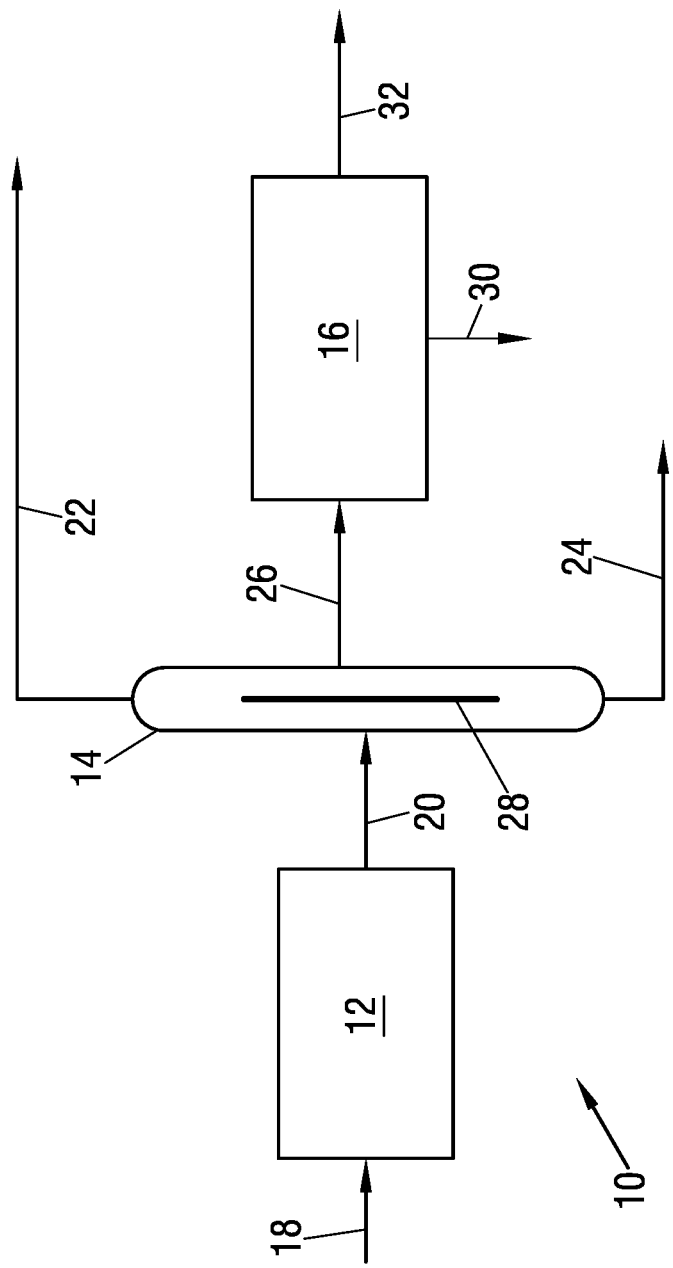
FIG. 1 is a diagrammatic illustration of a plant in accordance with one embodiment of the present invention.
Figure 2:
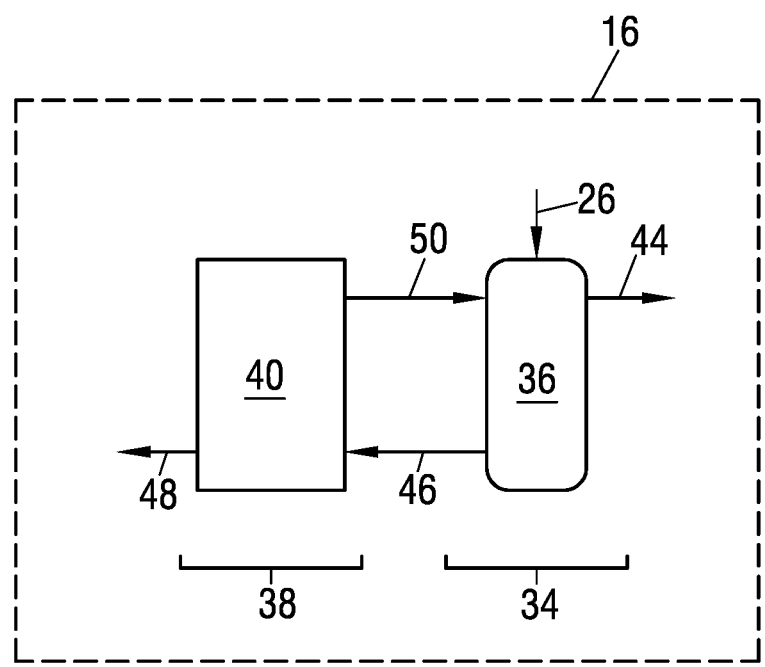
FIG. 2 is a diagrammatic illustration of a crystal block used in a method in accordance with one embodiment of the present invention.

FIG. 2 shows an embodiment of a crystallization block 16 for conducting the process for preparing a purified styrene composition in accordance with an embodiment of the present invention, such as in a plant as shown in FIG. 1. The crystallization block 16 includes a first dynamic melt crystallization section 34 which comprises one falling film crystallization stage or one falling film crystallizer 36, respectively as a dynamic melt crystallization stage or crystallizer, respectively. In addition, the crystallization block 16 comprises a second static melt crystallization section 38 having one static melt crystallization stage 40 or one static melt crystallizer, respectively. The falling film crystallizer 36 is connected with an inlet conduit 26 for side hydrocarbon stream obtained in the divided-wall column. In addition, the falling film crystallizer 36 has a discharge conduit 44 for the discharge of a purified styrene composition from the falling film crystallizer 36 and from the crystallization block 16. The static melt crystallizer 40 is connected with the falling film crystallizer 36 via a transfer conduit 46 which is suitable for transferring a first styrene depleted residue fraction obtained by crystallization in the falling film crystallizer 36 into the static melt crystallizer 40. With this respect, the transfer conduit 46 is in fluid communication with both the falling fain crystallizer 36 and the static melt crystallizer 40. The static melt crystallizer 40 comprises a discharge conduit 48 which serves for discharging a second styrene depleted residue fraction, which is obtained by the crystallization in the static melt crystallizer 40, from the static melt crystallizer 40 and from the crystallization block 16. A recycle conduit 50 provides a fluid communication between the static melt crystallizer 40 and the falling film crystallizer 36 and therefore allows to recycle at least a part of the second styrene enriched crystallization composition, which results from the crystallization in the static melt crystallizer 40, back into the falling film crystallizer 36.

Figure 3:
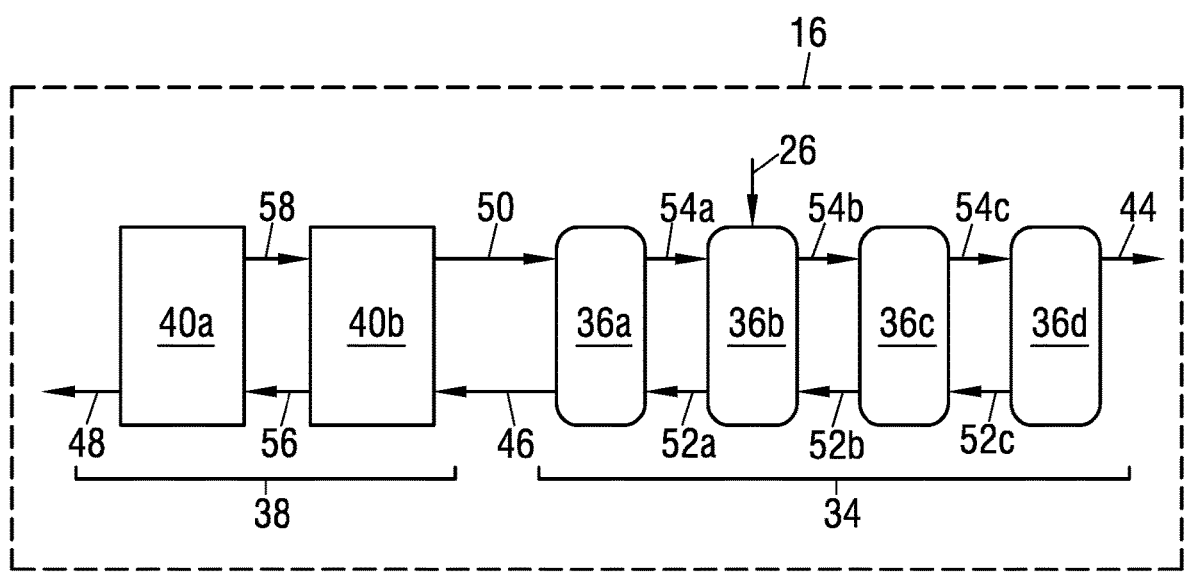
FIG. 3 is a diagrammatic illustration of a crystal block used in a method and plant in accordance with another embodiment of the present invention.

In FIG. 3, another embodiment of a crystallization block 16 for conducting the method for preparing a purified styrene composition in accordance with an embodiment of the present invention is shown. The first dynamic melt crystallization section 34 comprises four falling film crystallization stages 36a, 36b, 36c, 36d and the second static melt crystallization section 38 includes two static melt crystallization stages 40a, 40b. There are provided transfer conduits 52a, 52b, 52c between the falling film crystallization stages 36a, 36b, 36c, 36d, through which a styrene depleted residue fraction obtained by falling film crystallization in the single falling film crystallization stages 36a, 36b, 36c, 36d can be transferred from one of the falling film crystallization stages 36b, 36c, 36d to the respective upstream falling film crystallization stages 36a, 36b, 36c. In addition, the falling film crystallization stages 36a, 36b, 36c, 36d are connected via recycle conduits 54a, 54b, 54c suitable for recycling at least a part of the styrene enriched crystallized fractions obtained by falling film crystallization in the single falling film crystallization stages 36a, 36b, 36c, 36d from one of the falling film crystallization stages 36a, 36b, 36c to the respective downstream falling film crystallization stages 36b, 36c, 36d. An inlet conduit 26 for the side hydrocarbon stream obtained in the divided-wall column is connected to the second falling film crystallization stage 36b such that a crude styrene containing composition can be introduced into the second falling film crystallization stage 36b. A discharge conduit 44 is provided at the most downstream falling film crystallization stage 36d in order to remove the purified styrene composition from the crystallization block 16, A transfer conduit 46 provides a fluid communication between the most upstream falling film crystallization stage 36a of the first dynamic melt crystallization section 34 and the most upstream static melt crystallization stage 40b of the second static melt crystallization section 38 so that the styrene depleted residue fraction obtained by the crystallization in the falling film crystallization stage 36a can be transferred into the static crystallizer 40b of the second static melt crystallization section 38. The static melt crystallization stages 40a and 40b are connected via a transfer conduit 56 for transferring the styrene depleted residue fraction obtained by crystallization from the static melt crystallization stage 40b to the static melt crystallization stage 40a. In addition, the static melt crystallization stage 40a and the static melt crystallization stage 40b are connected via a recycle conduit 58 allowing for transferring the styrene enriched crystallized fraction, which results from the crystallization in the static melt crystallization stage 40a, into the static melt crystallizer of the crystallization stage 40b. Furthermore, the static melt crystallization stage 40a comprises a discharge conduit 48 for discharging the styrene depleted residue fraction, which is obtained by crystallization in the static melt crystallization stage 40a, from the crystallization block 38. A recycle conduit 50 provides a fluid communication between the static melt crystallization stage 40b and the falling film crystallization stage 36a and therefore allows to recycle at least a part of the styrene enriched crystallized fraction obtained in the static melt crystallization stage 40b of the second static melt crystallization section 38 back into the falling film crystallization stage 36a of the first dynamic melt crystallization section 34.

During operation of the crystallization block 16 shown in FIG. 3 a side hydrocarbon stream obtained in the divided-wall column is fed into the falling film crystallization stage 36b via the inlet conduit 26. In each of the falling film crystallization stages 36a, 36h, 36c, 36d a styrene enriched crystallized composition and a styrene depleted residue fraction are prepared. Each of the styrene depleted residue fractions obtained in one of the falling film crystallization stages 36b, 36c, 36d is transferred via the transfer conduits 52a, 52b, 52c to the respective upstream falling film crystallization stage 36a, 36h, 36c. In addition, each of the styrene enriched fractions obtained in one of the falling film crystallization stages 36a, 36b, 36c is at least partially recycled via the recycle conduits 36a, 36b, 36c to the respective downstream falling film crystallization stage 36b, 36c, 36d. The styrene depleted residue fraction obtained after the crystallization in the falling film crystallization stage 36a of the first dynamic melt crystallization section 34 is transferred via the transfer conduit 46 into the static melt crystallization stage 40b of the second static melt crystallization section 38, The styrene depleted residue fraction obtained in the static melt crystallization stage 40b is transferred via the transfer conduit 56 to the downstream static melt crystallization stage 40a, in addition, the styrene enriched crystallized fraction obtained in the static melt crystallization stage 40a is at least partially recycled via the recycle conduit 58 into the upstream static melt crystallization stage 40b. The styrene enriched crystallized fraction obtained after the crystallization in the static melt crystallization stage 40b is recycled via the recycle conduit 50 into the falling film crystallization stage 36a of the first dynamic melt crystallization section 34. A finally purified styrene composition obtained in the crystallization stage 36d is removed from the crystallization block 16 via the discharge conduit 44, while the final styrene depleted residue fraction is removed from the static melt crystallization stage 40a and from the crystallization block 16 via the discharge conduit 48.

In accordance with an embodiment of the present invention, Table 2 lists the different impurities that can be typically present in a crude hydrocarbon stream containing styrene and in the side hydrocarbon stream obtained in the divided-wall column with their melting points. The reason for impurities removal from side hydrocarbon stream obtained in the divided-wall column by crystallization block 16 is twofold: a) Some of the species have melting points lower than styrene and b) during the crystallization process, impurities which have higher melting point are more soluble in the mother liquor. Thus, despite having a higher melting point, these impurities can be removed from styrene by crystallization. Increasing product purity is directly correlated with an increasing number of crystallization stages. Recovery, on the other hand, is a function of the number of residue stages.

TABLE 2

| COMPOUND | MELTING POINT | |
| --- | --- | --- |
| Water | 0° C. | (32° F.; 273K) |
| α-Methylstyrene | −23° C. | (−9.4° F.; 250K) |
| o-Xylene | −25.2° C. | (−13.4° F.; 248K) |
| Benzaldehyde | −26° C. | (−14.8° F.; 247K) |
| Styrene | −30.6° C. | (−23.1° F.; 243K) |
| Thiophenic compounds boiling in the range 130-150° C. | −65 to −30° C. | (−85 to −22° F.; 208 to 243K) |
| Phenylacetylene | −45° C. | (−49° F.; 228K) |
| Ethylbenzene | −95° C. | (−139° F.; 178K) |
| 3-Ethyltoluene (m-ethyltoluene) | −95.5° C. | (−140° F.; 177.6K) |
| Cumene | −96° C. | (−141° F.; 177K) |
| n-Propylbenzene | −99.5° C. | (−147° F.; 173.7K) |

The invention claimed is:

1. A method for preparing a purified styrene composition, the method comprising:
   providing a crude hydrocarbon composition containing styrene,
   subjecting the crude hydrocarbon composition to a distillation in a divided-wall column to produce an overhead hydrocarbon stream, a bottom hydrocarbon stream, and a side hydrocarbon stream and
   subjecting the side hydrocarbon stream to at least one crystallization step to obtain a purified styrene composition.

2. The method of claim 1, wherein the crude hydrocarbon composition is subjected to distillation in a middle divided-wall column.

3. The method of claim 1, wherein the overhead hydrocarbon stream is a $C_{7-}$-hydrocarbon stream, the bottom hydrocarbon stream is a $C_{9+}$-hydrocarbon stream and the side hydrocarbon stream is a styrene containing hydrocarbon stream.

4. The method of any of claim 1, wherein the side hydrocarbon stream is subjected to at least one crystallization step containing at least 80% by weight of styrene.

5. The method of claim 1, wherein the crude hydrocarbon composition and the side hydrocarbon stream contain one or more impurities selected from the group consisting of color inducing species, sulfur species, meta- and ortho-xylenes, ethylbenzene, phenylacetylene, cumene, n-propylbenzene, alpha-methylstyrene, ethyltoluene, organo-chlorinated, organo-nitrogenated species and arbitrary mixtures of two or more of the aforementioned impurities.

6. The method of claim 5, wherein the crude hydrocarbon composition and the side hydrocarbon stream contain as impurities one or more sulfur species and preferably one or more sulfur species selected from the group consisting of mercaptans, disulfides, thiophenes having a boiling point of 130 to 150° C. and arbitrary combinations of two or more thereof.

7. The method of claim 5, wherein the crude hydrocarbon composition and the side hydrocarbon stream contain as impurities one or more color inducing species comprising at least one of conjugated diolefins, oxygenated species, and oxygenated sulfur species.

8. The method of claim 5, wherein the at least one crystallization step comprises at least one static melt crystallization stage and at least one dynamic melt crystallization stage, wherein the at least one dynamic crystallization stage is a falling film melt crystallization stage.

9. The process according to claim 5, wherein the crude hydrocarbon composition is a pygas obtained by pyrolyzing an ethylbenzene and styrene containing stream produced in an ethyl-benzene/styrene monomer (EBSM) process, by pyrolyzing a hydrocarbon stream obtained in a naphtha cracker, or by pyrolyzing polystyrene.

10. The method of claim 5, wherein the purified styrene composition has a styrene content of at least 99.00% by weight.

11. The method of claim 5, wherein the purified styrene composition bears at least one of the following properties:
   has a color of maximum 15 as defined by Pt-Co scale as per ASTM D5386,
   comprises less than 2 ppmw of total elemental sulfur as contained in mercaptans, disulfides and thiophenes,
   comprises less than 20 ppmw of oxygenates,
   comprises less than 40 ppmw of impurities selected from the group consisting of phenylacetylene, mixed xylenes, ethylbenzene, cumene, ethyltoluene, n-propylbenzene, and alpha-methylstyrene,
   has polymer content of less than 10 ppmw, and
   has total organic chlorine content of less than 2 ppmw.

12. A plant for preparing a purified styrene composition comprising:
   at least one divided-wall column; and
   at least one crystallization block, the divided-wall column comprising an inlet line for a crude hydrocarbon composition containing styrene, a line for overhead hydrocarbon stream, a line for bottom hydrocarbon stream and a line for side hydrocarbon stream, the at least one crystallization block comprising an inlet line, the line for side hydrocarbon stream of the divided-wall column being the inlet line of the at least one crystallization block, and the at least one crystallization block comprising two or more static crystallization stages and two or more dynamic crystallization stages.

13. The plant of claim 12, wherein the divided-wall column is a middle divided-wall column, wherein the dividing wall of the middle divided-wall column extends, seen over a middle divided-wall column height, which is the straight distance between the bottom and the top of the middle divided-wall column, essentially vertically downwards from 10 to 90% of the height of the middle divided-wall column, wherein essentially vertically downwards means that the angle between the dividing wall and the length axis of the middle divided-wall column is at most 20°.

14. The plant of claim 12, further comprising a pyrolysis or catalytic reactor unit block comprising an inlet line and an outlet line, wherein the outlet line of the pyrolysis or catalytic reactor unit block is an inlet line for the divided-wall column.

15. The plant of claim 12, wherein the crystallization block comprises
   at least one static crystallization section comprising a plurality of static crystallization stages,
   at least one dynamic crystallization section comprising a plurality of dynamic crystallization stages and
   at least two conduits that fluidly couple at least one of the plurality of static crystallization stages with at least one of plurality of dynamic crystallization stages, wherein one of the at least two conduits fluidly couples one of the plurality of static crystallization stages with one of the plurality of dynamic crystallization stages so that a styrene depleted residue fraction obtained in one of the plurality of the dynamic crystallization stages may be fed into one of the plurality of the static crystallization stages being fluidly coupled with one of the plurality of the dynamic crystallization stages, and wherein one of the at least two conduits fluidly couples one of the plurality of the static crystallization stages with one of the plurality of the dynamic crystallization stages being fluidly coupled with one of the plurality of the static crystallization stages so that a styrene enriched crystallized fraction obtained in one of the plurality of the static crystallization stages may be fed into one of the plurality of the dynamic crystallization stages.

16. The method of any of claim 1, the side hydrocarbon stream is subjected to at least one crystallization step containing at least 99% by weight of styrene.

17. The method of claim 5, the purified styrene composition has a styrene content of at least 99.98% by weight.

18. The plant of claim 12, wherein the divided-wall column is a middle divided-wall column, the dividing wall of the middle divided-wall column extends, seen over a middle divided-wall column height, which is the straight distance between the bottom and the top of the middle divided-wall column, essentially vertically downwards from 10 to 90% of the height of the middle divided-wall column, essentially vertically downwards means that the angle between the dividing wall and the length axis of the middle divided-wall column is at most 0°.

* * * * *